United States Patent [19]
Morgentaler

[11] Patent Number: 5,224,953
[45] Date of Patent: Jul. 6, 1993

[54] METHOD FOR TREATMENT OF OBSTRUCTIVE PORTIONS OF URINARY PASSAGEWAYS

[75] Inventor: Abraham Morgentaler, Chestnut Hill, Mass.

[73] Assignee: The Beth Israel Hospital Association, Boston, Mass.

[21] Appl. No.: 877,412

[22] Filed: May 1, 1992

[51] Int. Cl.$^5$ .............................................. A61M 29/00
[52] U.S. Cl. ..................................... 606/192; 604/53; 623/12
[58] Field of Search ................. 623/1, 12; 604/53, 54; 606/108, 191, 192

[56] References Cited

U.S. PATENT DOCUMENTS

| | | | |
|---|---|---|---|
| 4,425,908 | 1/1984 | Simon | 128/1 R |
| 4,512,338 | 4/1985 | Balco et al. | 128/1 R |
| 4,553,545 | 11/1985 | Maass et al. | 128/341 |
| 4,580,568 | 4/1986 | Gianturco | 128/345 |
| 4,655,771 | 4/1987 | Wallsten | 623/1 |
| 4,733,665 | 3/1988 | Palmaz | 606/191 |
| 4,739,762 | 4/1988 | Palmaz | 128/343 |
| 4,768,507 | 9/1988 | Fischell et al. | 128/303 R |
| 4,830,003 | 5/1989 | Wolff et al. | 128/343 |
| 4,886,062 | 12/1989 | Wiktor | 128/343 |
| 4,969,458 | 11/1990 | Wiktor | 606/194 |
| 5,026,377 | 6/1991 | Burton et al. | 606/108 |
| 5,034,001 | 7/1991 | Garrison | 604/53 |
| 5,178,618 | 1/1993 | Kandarper | 606/198 |

OTHER PUBLICATIONS

Wm. J. Buehler, et al. "A Summary of Recent Research On The Nitinol Alloys . . . ", 1968, pp. 105–118.
Julio C. Palmaz, et al. "Expandable Intraluminal Graft: A Preliminary Survey", Jul., 1985.
Ulrich Sigwart, et al. "Intravascular Stents . . . ", Mar. 19, 1987 New England Journal of Medicine, vol. 316, No. 12 pp. 701–706.
Gerard Duprat, Jr., et al. "Self-expanding Metallic Stents . . . " Feb., 1987. International Radiology vol. 162 pp. 469–472.
Josef Rosch, et al. ". . . Use of Expandable Gianturco Stents" Feb., 1987 Radiology vol. 162 pp. 481–485.
David D. Lawrence, Jr., et al. "Percutaneous Endovascular Graft . . . " May, 1987.
C. L. Zollikofer, et al. "Endovascular Stenting of Veins and Grafts . . . " Jun., 1988.
Herve Rousseau, et al. "Self-expanding Endovascular Prosthesis . . . " Sep., 1987, Radiology.
David Mirich, et al. "Percutaneously Placed Endovascular Grafts . . . " Mar. 1989.
Cook, Inc., "Gianturco—Roehm Bird's Nest Vena Cava Filter" 1989.
Gary J. Becker, "Intravascular Stents" Feb., 1991.

Primary Examiner—J. L. Kruter
Attorney, Agent, or Firm—Lorusso & Loud

[57] ABSTRACT

A method for the treatment of an obstructive portion of a urinary passageway of a mammal, comprising the steps of providing a stent thermally self-movable between a first condition in which the stent is rigid and generally tubular, and a second condition in which the stent is flexible and compressible, moving the stent in the second condition through a catheter to the obstructive portion of the urinary passageway while maintaining the stent in its second condition by flowing a cool solution through the stent, moving the stent out of the catheter and into the obstructive portion of the urinary passageway, and discontinuing the flow of cool solution, whereby the stent is caused by body temperature, or by the flow of a warm solution, to assume its first condition to hold open the obstructive portion of the urinary passageway.

26 Claims, 2 Drawing Sheets

METHOD FOR TREATMENT OF OBSTRUCTIVE PORTIONS OF URINARY PASSAGEWAYS

BACKGROUND OF THE INVENTION

1. Field of the Invention

This invention relates to treatment of obstructive portions of urinary passageways and is directed more particularly to a non-surgical method of treating obstructive strictures and segments of the urethra and ureter.

2. Description of Prior Art

It is known that obstruction of the urinary tract often is caused by the prostate gland enlarging, bearing against the urethra, reducing the urethral lumen and restricting urine flow. An enlarged prostate gland causes a number of symptoms urinary hesitancy or urgency, stranguria and post-void dribbling, as well as bladder stones and recurrent infections. Generally, patients suffering from such symptomatic prostatism may pursue one of the several treatments: undergo surgical prostatectomy, have inserted in the prostatic urethra an indwelling catheter, or receive intermittent treatment with a urethral catheter. In recent times, in some countries, a further alternative has been to have inserted in the prostatic urethra a coil stent.

Surgery subjects the patient to a number of hazards, such as post-operative bleeding, stricture formation at the urethra or bladder neck, incontinence, bladder spasm, urinary infection, reactive urethral swelling causing urinary obstruction, and epididymitis. Other risks include wound infection, retention of prostatic chips, retrograde ejaculation, bladder perforation, hyponatremia, intravascular hemolysis, and impotency. Furthermore, surgery requires about 1 to 2 hours in the operating room, plus an average of 3-5 days in the hospital (or more in complicated cases). About 10-15% of prostatectomy patients eventually require a repeat prostatectomy and probably 10% develop strictures with long-term costs.

Long term indwelling bladder catheterization to keep the urethra open carries a significant risk of infection. Frequent catheter changes may be made to prevent poor drainage due to blockage by encrustation.

Intermittent treatments by means of urethral catheter are normally performed by the patients themselves. Such self-treatment, involving moving a catheter through the urethra to the bladder, for many patients, particularly for the aged, is difficult or impossible.

A coil stent has been used experimentally in place of the indwelling catheter, with some success and several complications. The coil stent is also known as the spiral urethral prosthesis and as the Prostakath prostatic stent. The coil stent has a spring-like main body that remains in the prostatic urethra with a tapered end for easy insertion, a straight section which remains in the sphincter muscle area, and a distal coil which remains in the bulbar urethra to allow adjustment. While the coil stent re-establishes voiding in some patients, the stent causes a number of complications. The tapered end of the coil stent protrudes into the interior of the bladder, and may cause discomfort and bladder irritability. The coil stent can migrate into the bladder, since only the enlarged prostate gland provides the force keeping the coil stent in place. The distal coil may perforate the bulbar urethra. Finally, the voiding rates have been only marginally improved.

It would, therefore, be beneficial to the medical arts to have available a method for treatment of obstructive prostatism which avoids surgery, the insertion of an indwelling catheter, and treatment, intermittent and permanent, with a urethral catheter, and their attendant problems. It would further be beneficial to have available a method for treatment of obstructive prostatism utilizing the placement of a stent in the prostatic portion of the urethra, but a stent having superior characteristics relative to the coil stent, and, in particular, a stent which may be easily positioned and repositioned. It would further be beneficial to have available a like method for treatment of obstructive segments and strictures of the ureter.

SUMMARY OF THE INVENTION

Accordingly, an object of the present invention is to provide a method for treatment of obstructive segments and strictures of the urethra and ureter, including obstructive prostatism, which method avoids the risks and problems associated with surgery, indwelling catheters and urethra catheters.

A further object of the present invention is to provide such a method utilizing a stent, but avoiding the problems attendant with use of the coil stent.

A still further object is to provide a method utilizing a stent, which method includes, when desired, repositioning of the stent after the stent is fully set in place.

With the above and other objects in view, as will hereinafter appear, a feature of the present invention is the provision of a method for treatment of an obstructive portion of a urinary passageway of a mammal, the method comprising of the steps of measuring the length of the obstructive portion of the passageway, providing a stent adapted to assume a first condition when exposed to body temperature of the mammal, and adapted to assume a second condition when exposed to a transition temperature less than the body temperature, the stent in the first condition being rigid and generally tubular in configuration, and having a selected length approximately equal to the measured length of the obstructive portion, and in the second condition being flexible and compressible to a size substantially smaller in diameter than the size of the stent in the first condition, disposing the stent in the passageway in said obstructive portion, flowing a cool solution through the stent, the cool solution being of a temperature no greater than the transition temperature, and discontinuing the flow of cool solution whereby the stent is caused by the body temperature to assume the first condition to hold open the obstructive portion.

In accordance with a further feature of the invention, there is provided a method for the treatment of obstructive urethral segments and strictures in a mammal, the method comprising the steps of measuring the obstructive portion of the urethra, providing a stent adapted to assume a first condition when exposed to body temperature of the mammal, and adapted to assume a second condition when exposed to a transition temperature less than the body temperature, the stent in the first condition being rigid and generally tubular in configuration, and having a selected length approximately equal to the measured length of the obstructive portion, and in the second condition being flexible and compressible to a size substantially smaller in diameter than the size of the stent in the first condition, inserting the stent in the second condition into a catheter, moving the stent to a distal end of the catheter, inserting the catheter in the urethra to position the stent in the obstructive portion of the urethra, flowing a cool solution through the catheter, the cool solution being at a temperature no greater than the transition temperature, moving the stent out of the catheter and into the obstructive portion of the urethra, and discontinuing the flow of the cool solution through the catheter, whereby the stent is caused by the body temperature to assume the first condition to hold open the urethra obstructive portion.

In accordance with a still further feature of the invention, there is provided a method for treatment of obstructive ureteral segments and strictures in a mammal, the method comprising the steps of measuring the length of the obstructive portion of the ureter, providing a stent adapted to assume a first condition when exposed to body temperature of the mammal, and adapted to assume a second condition when exposed to a transition temperature less than the body temperature, the stent in the first condition being rigid and generally tubular in configuration, and having a selected length approximately equal to the measured length of the obstructive portion, and in the second condition being flexible and compressible to a size substantially smaller in diameter than the size of the stent in the first condition, extending a wire between a bladder at a first end of the ureter and a renal pelvis at a second end of the ureter, said wire extending through said obstructive portion of the ureter, placing a catheter with the stent therein in the second condition around the wire, moving the catheter along the wire until the catheter is disposed in the obstructive portion of the ureteral, flowing a cool solution at a temperature no greater than the transition temperature through the catheter and through the stent to maintain the stent in the second condition, separating the catheter from the stent, terminating the flow of cool solution, and withdrawing the catheter and the wire from the ureter, leaving the stent in the obstructive portion of the ureter, whereby the stent is caused by the body temperature to assume the first condition to hold upon the obstructive portion of the ureter.

In accordance with a still further feature of the invention, there is provided a method for treatment of obstructive ureter segments and strictures in a mammal, the method comprising the steps of moving a ureteroscope into a ureter and through the ureter to gain visual access to the obstructive portion of the ureter, visually measuring the length of the obstructive portion of the ureter, directly or with the aid of contrast radiographs, providing a stent adapted to assume a first condition when exposed to body temperature of the mammal, and adapted to assume a second condition when exposed to a transition temperature less than the body temperature, the stent in the first condition being rigid and generally tubular in configuration, and having a selected length approximately equal to the measured length of the obstructive portion, and in the second condition being flexible and compressible to a size substantially smaller in diameter that the size of the stent in the first condition, placing the stent in the second condition in a catheter, passing the catheter with the stent therein through a working channel of the ureteroscope until a distal end of the catheter is at or beyond a furthest boundary of the obstructive portion, expelling the stent from the catheter and into the ureter in the obstructive portion, whereby the stent is caused by the body temperature to assume the first condition to hold open the ureter obstructive portion.

In accordance with a further feature of the invention, upon discontinuing of the flow of the cool solution, a flow of warm solution, at a temperature sufficient to cause the stent to assume its first condition, is initiated to quicken the stent's assumption of the first condition.

In accordance with a still further feature of the invention, the stent, if initially placed somewhat off target, may be moved to a second location in the area of the obstructive portion of the urethra or ureter by again subjecting the stent to the flow of cool solution to render the stent flexible, moving the stent, as by endoscopic forceps, or other grasping tools, and again discontinuing the flow of cool solution, to cause the stent to be warmed by body temperature (and flow of warm solution, if desired) whereupon the stent resumes its first condition.

The above and other features of the invention, including various novel details of construction and combinations of parts, will now be more particularly described with reference to the accompanying drawings and pointed out in the claims. It will be understood that the particular methods embodying the invention are shown and described by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DESCRIPTION OF THE PREFERRED EMBODIMENT

In accordance with the inventive method, an operator first obtains a measurement of the length of an obstructive portion, such as, for example, the prostatic portion of the urethra. This may be done in a manner taught by Kleih U.S. Pat. No. 4660,560, in which a multichannel cystoscope is inserted into the urethra. The cystoscope is moved into the urethra so as to dispose a distal end of the cystoscope proximate, or in, the bladder. A calibrated catheter is then passed through the cystoscope until a distal end of the catheter progresses to the bladder neck. By viewing the calibrated catheter through the cystoscope, an operator determines the number of calibrations between the veru montanum and the bladder neck, thereby determining the length of the prostatic portion of the urethra.

Once the length of the prostatic portion of the urethra is known, a stent of proper length may be selected. The stent used in the methods described herein preferably is the type shown and discussed in U.S. patent application Ser. No. 07/878,184 filed concurrently with this application, in the name of Morris Simon, et al.

Figure 1:
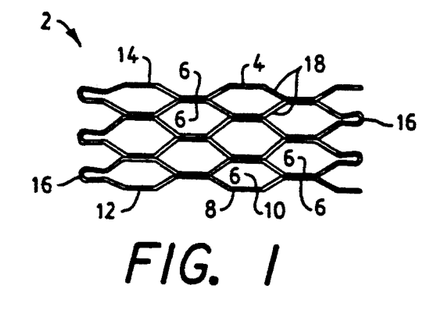
FIG. 1 is a diagramatic side elevational view of a stent used in the practice of the inventive methods, the stent being shown in a first condition.

The stent includes a skeletal frame 2, preferably formed from a single wire 4. The wire 4 includes a plurality of straight portions 6 which are joined to each other, as by welding.

In FIG. 1, the illustrative stent is shown in a first condition in which the frame 2 is expanded, relatively rigid, and substantially tubular in configuration. The ends 8, 10 of the single wire 4 are disposed in one of the welded straight portions 6, such that there are no exposed wire free ends, disposed within or extending from the frame 2. The wire 4 preferably is round in cross-section. In the frame straight portions 6 the joined wire segments are disposed, relative to the tubular configuration of the frame, circumferentially thereof. The wire 4 abuts itself only at the straight portions 6 and does not cross itself at any point. Accordingly, the frame walls, that is, walls 12 of a tubular body portion 14 of the frame 2 have a thickness equal to the diameter of the wire 4.

The stent includes the body portion 14 and finger portions 16 extending generally axially from one, or both, ends of the body portion. The fingers facilitate a gradual reduction in radially outwardly extending pressure exerted by the stent on the wall of a urinary passageway in which the stent is located. Such gradual reduction of pressure facilitates acceptance of the stent by the passageway and reduces deleterious reactions by the wall of the passageway to the presence of the stent.

The tubular body portion 14 comprises a mesh formed by the wire 4, the mesh comprising a plurality of interconnected cells 18 of a polygonal configuration when viewed in plan, providing straight sides to form the aforementioned straight potions 6. The polygonal cells 18 preferably are of a hexagonal configuration, which readily provides expansion and rigidity characteristics desirable in the structure and operation of the device. The portion of the stent having the mesh construction exercises a substantially greater radial bias than do the finger portions 16.

The stent preferably is made of a known alloy of nickel and titanium which provides the stent with thermal memory. The unique characteristic of the alloy, known generally as "Nitinol", is its thermally triggered shape memory, which allows the stent constructed of the alloy to be loaded into a catheter in a relatively compressed and elongated state, and regain a useful shape at a selected temperature, such as human body temperature. The two interchangeable shapes are possible because of the two distinct crystalline structures that are interchangeable with a small variation in temperature. The temperature at which the stent assumes its first condition may be varied within wide limits by changing the composition of the alloy. Thus, while for human use the alloy may be focused on a body temperature of 98.6° F., the alloy readily may be modified for use in animals with different body temperatures.

Figure 2:
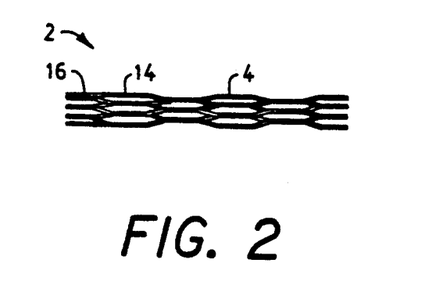
FIG. 2 is a diagramatic side elevational view of the stent shown in FIG. 1, but shown in a second condition.
Figure 3:
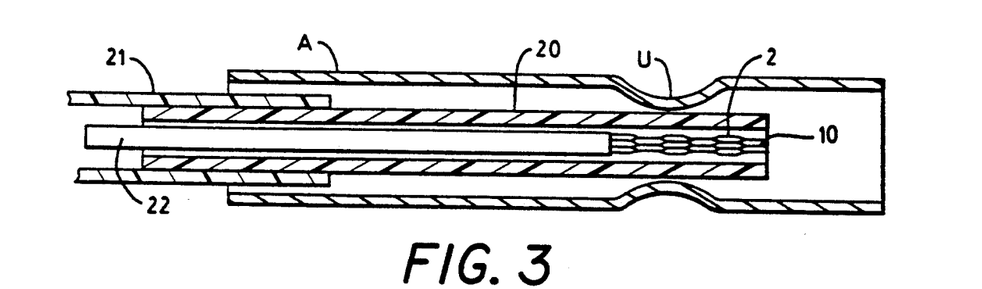
FIGS. 3-5 illustrate diagramatically steps in one inventive method described herein.

Accordingly, when the stent shown in FIG. 1 is subjected to a transition temperature, the relatively rigid stent changes to a second condition in which it is flexible, stress-free and collapsible. The stent does not, of its own accord, collapse, or compress, but the stent does become quite collapsible and compressible. By mechanical means, the stent may be compressed to a point at which the walls 12 of the body portion 14 of the stent frame 2 are positioned against each other, to form a stent diameter substantially equal to the combined thickness of the frame walls in abutting engagement with each other. In FIG. 2, the stent is shown in a compressed condition approaching, but not having yet reached, the fully compressed condition in which the walls of the stent abut each other. In the fully compressed condition, the stent is readily contained by a catheter 20 (FIG. 3).

The ratio of expanded stent diameter to compressed stent diameter can be controlled within limits by selection of wire diameter. In general, the greater the diameter of the wire 4, the greater the ratio of the stent expanded diameter. By selection of wire diameter, the maximum expanded stent diameter may be selected and thereby the radial force which the expanded stent exerts on the interior walls of the tract or passageway in which the stent is set. The diameter of the expanded stent generally is on the order of 6 to 10 times the diameter of the compressed stent.

The stent described above, in accordance with the present method, is inserted into the catheter 20 (FIG. 3) with the stent in its second condition. In its flexible, stress-free state the stent is moved within the catheter by use of a pusher member 22 to a distal end of the catheter 20. The catheter is then placed within a multi-channel cystoscope 21 and moved through the cystoscope to position the stent in the prostatic portion U of the urethra.

To maintain the stent in its second condition a cool solution, such as a saline solution, may be flowed through the catheter 20. The cool solution is of a temperature, which is at or below the transition temperature, that is, the temperature at which the stent assumes its relaxed condition.

Figure 4:
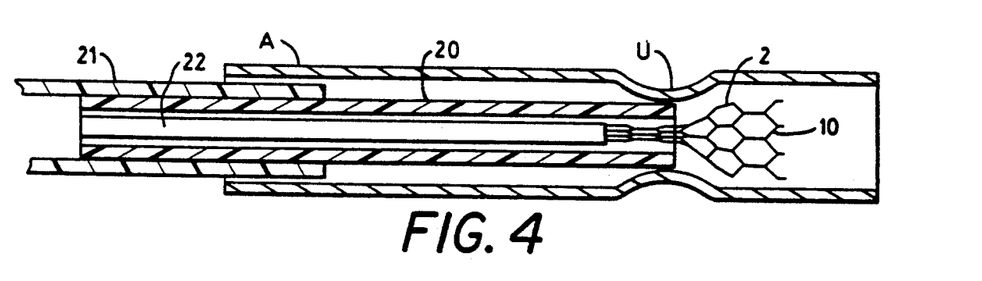
Figure 5:
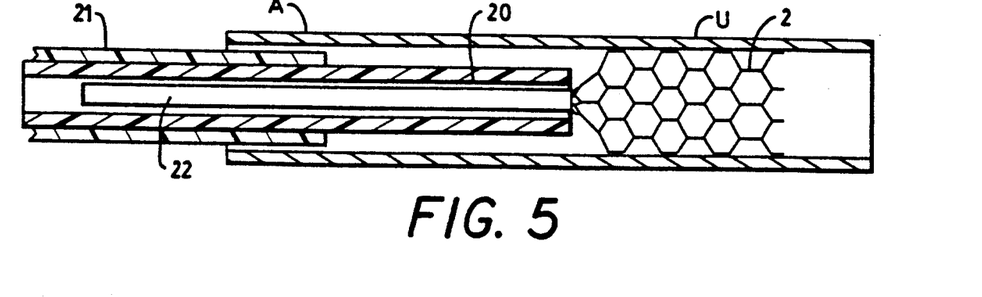

When the position of the stent in the prostatic portion of the urethra is deemed appropriate, the stent is moved out of the catheter 20 by the pusher member 22 and into the urethra (FIG. 4). As the stent is moved from the catheter, the flow of cool solution is discontinued. Exposure of the stent to body temperature causes the stent to warm and change from the second condition to the expanded and relatively rigid first condition, urging the walls of the urethra outwardly against the inwardly directed pressure of the prostate (FIGS. 4 and 5). If desired, the flow of a warm solution through the catheter may be started after discontinuance of the flow of cool solution, to assist in rapidly warming the stent to the temperature at which the stent assumes its first condition. Thus, the temperature of the warm solution is typically equal to, or in excess of, the relevant body temperature.

Upon completion of the above-described exercise, the stent is disposed in the prostatic portion of the urethra, the stent being in its first condition and operative to hold open the urethra (FIG. 5).

In some instances, it is discovered after the placement of the stent that its disposition is somewhat removed from the preferred location. In such instances, the stent may again be subjected to the flow of cool solution, causing the stent to assume its second condition. With the stent flexible and stress-free, the stent may be moved, as by endoscopic forceps, to a second location and the flow of cool solution stopped. Again, if desired, a warm solution may be flowed past the stent to expedite the stent's assuming the first condition. Either through body temperature, or body temperature in combination with warm solution, the stent is warmed and again assumes its first condition, but in a second location.

Thus, in addition to facilitation of treatment of obstructive prostatism, the present method contemplates checking the position of the set stent and, if desirable, moving the stent to an improved location.

When the stent is located in the urethra, the cystoscope and catheter are withdrawn, leaving the stent in place, If subsequently, there is migration of the stent into the bladder, the stent may again be made to assume its relaxed state, to facilitate movement of the stent within the urethra.

In a related disorder of the urinary system, obstructive segment or stricture of the ureter, procedures similar to the above-described procedures may be used to stent the affected passageway, to permit flow of urine therethrough. Whereas the above-described procedures pertain to flow from the bladder, through the urethra, the procedures described hereinbelow pertain to flow from the kidneys to the bladder through the ureter.

Figure 6:
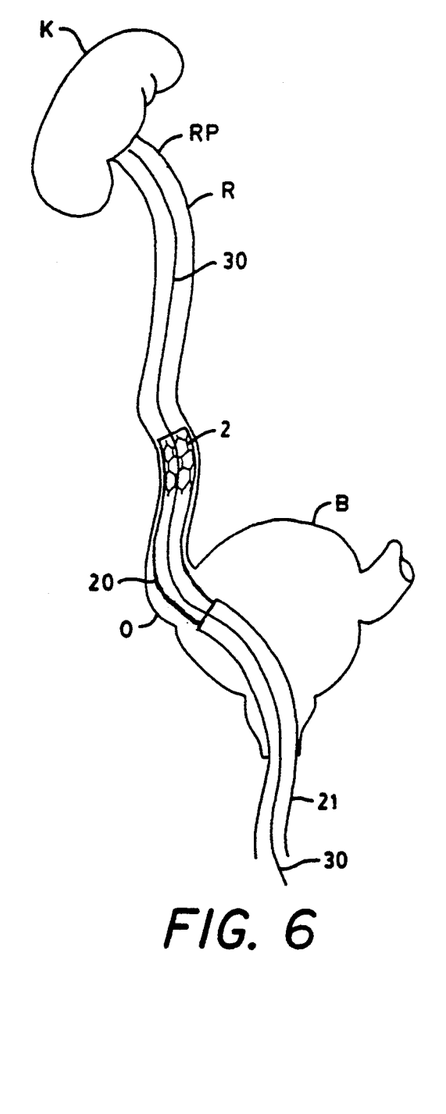
FIG. 6 is a diagrammatic representation of a method for stenting another area of the urinary tract.

In one embodiment, illustrated in FIG. 6, a stent 2 of the type described above is placed in the ureter R with the aid of fluoroscopy. A pyeloureterogram may be performed to identify and measure the area of the ureter to be stented. An appropriate length stent is selected, based upon the measured length of the affected area.

A wire 30 is passed into the ureter R and extends therethrough between a renal pelvic portion RP of a kidney K and a ureteral orifice O of the Bladder B, the wire 30 extending through the affected portion of the ureter R. The wire 30 may be introduced to the ureteral orifice O by a cystoscope 21 and then extended therefrom u the ureter to the renal pelvis. If a nephrostomy tube is present, the wire may be passed antegrade to the bladder.

The selected stent 2 is then placed within a catheter 20, the stent 2 being in its second, or relaxed, condition. The stent 2 and catheter 20 are then fed over the wire 30 and extended along the length of the wire until the stent is disposed in the desired area. A cool solution, that is, a solution having a temperature no greater than the transition temperature of the stent, is flowed through the catheter and the stent to maintain the stent in its relaxed condition.

The stent is then separated from the catheter and the flow of cool solution stopped. Optionally, a warm solution, that is, solution at a temperature at which the stent transforms to its first, or rigid, condition, is flowed past the stent to assist the stent in rapid transition to the expanded and rigid state.

Fluoroscopy is used throughout the procedure to assist in proper positioning of the stent. However, if it is found after activation of the stent that for maximum effectiveness, the stent should be moved, flowing cool solution past the stent will cause the stent to assume its relaxed state, permitting easy movement of the stent by a grasping tool. After movement of the stent, the flow of cool solution is stopped, and the flow of warm solution started (if desired), to permit the stent to again assume its rigid condition. The stent is released by the grasping tool, which is withdrawn.

A repeat pyeloureterogram may be performed to confirm successful stenting.

While fluoroscopy is of value as an assist to stenting the ureter, it is not necessary. In an alternative method of stenting the ureter, illustrated diagrammatically in FIG. 7, visual access to the affected area is obtained by use of a ureteroscope 32, which is moved into the ureter R and through the ureter to the affected area. A measurement of the length of the affected area is taken visually and a proper length stent is selected. A catheter 20, having the stent 2 in relaxed condition therein, is passed through a working channel of the ureteroscope 32 until a distal end of the catheter 20 is at or beyond a furthest boundary of the obstructive portion of the ureter. In the course of positioning the catheter, a cool solution is flowed therethrough to maintain the relaxed condition of the stent.

Figure 7:
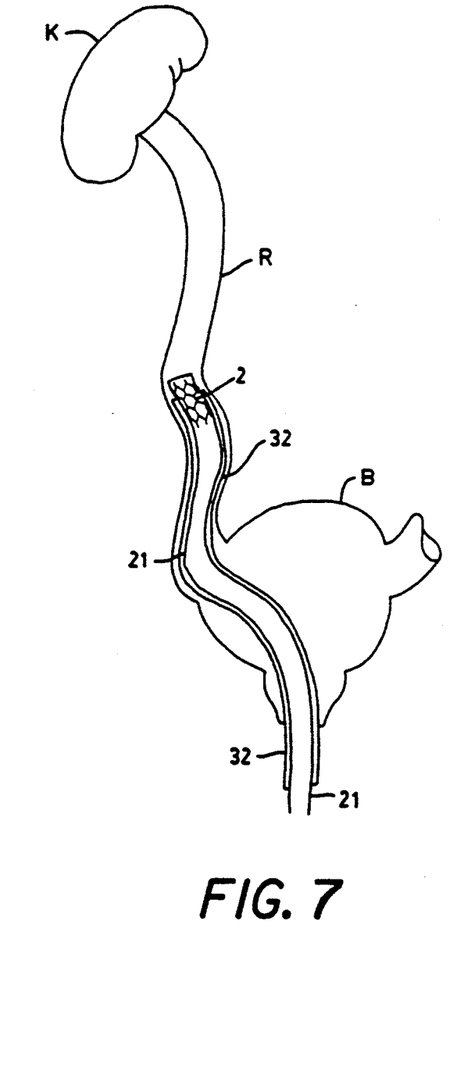
FIG. 7 is a diagrammatic representation of an alternative method for stenting the other area of the urinary tract.

The stent is then expelled into, and the catheter withdrawn from, the affected area, and the flow of cool solution stopped, Optionally, warm fluid may be flowed past the stent to assist in transition of the stent to its rigid state. After exposure to body temperature, and aided, if desired, by the flow of warm fluid thereby, the stent assumes its first, or rigid and expanded, condition.

As in the previously described embodiments, if relocation of the stent is required, the cool solution may be flowed through the ureteroscope and past the stent to relax the stent which may then be moved by endoscopic forceps, or other grasping tool. Upon completion of relocation, the flow of cool fluid is stopped and the stent reassumes its first condition.

Thus, there are provided methods for stenting portions of a urinary passageway comprising measuring the length of the affected portion, carrying a stent, as above described, through the passageway to a position in the affected area, while flowing a cool solution past the stent, separating the stent from its carrier and discontinuing the flow of cool fluid, whereby the stent reacts to body temperature to transform from a relaxed and compressed state to a rigid and expanded state in the passageway to keep open an otherwise obstructive portion of the passageway. To assist in rapid expansion of the stent, a warm solution may be flowed thereby. If the stent requires relocation, a cool solution is flowed through the stent and, after the stent has transformed to its relaxed state, the stent may be moved by a grasping tool. Discontinuing flow of the cool solution permits the stent, in response to body temperature, either alone or in conjunction with the flow of warm fluid, to resume its rigid state.

It is to be understood that the present invention is by no means limited to the particular construction and method steps herein disclosed and/or shown in the drawings, but also comprises any modifications or equivalents within the scope of the claims.

Having thus described my invention, what I claim as new and desire to secure by Letters Patent of the United States is:

1. A method for treatment of an obstructive portion of a urinary passageway of a mammal, said method comprising of the steps of:

measuring the length of said obstructive portion of said passageway, providing a stent adapted to assume a first condition when exposed to body temperature of said mammal, and adapted to assume a second condition when exposed to a transition temperature less than said body temperature, said stent in said first condition being rigid and generally tubular in configuration, and having a selected length substantially equal to the measured length of said obstructive portion, and in said second condition being flexible and compressible to a size substantially smaller in diameter than the size of said stent in said first condition, carrying said stent through said passageway to said obstructive portion, flowing a cool solution through a carrier containing said stent, said cool solution being of a temperature no greater than said transition temperature, separating said stent from said carrier in said passageway in said obstructive portion, and discontinuing said flow of said cool solution, whereby said stent is caused by said body temperature to assume said first condition to hold open said obstructive portion.

2. The method for treatment of an obstructive portion of a urinary passageway in accordance with claim 1, including the additional step of flowing warm solution through said stent after said stent has been disposed in said obstructive portion and after discontinuance of said flow of cool fluid through said stent, said warm solution being at a temperature sufficient to cause said stent to assume said first condition, whereby said stent is caused at least in part by said warm solution to assume said first condition to hold open said obstructive portion.

3. The method for treatment of an obstructive portion of a urinary passageway in accordance with claim 2, including the additional steps of flowing said cool solution through said stent to cause said stent to reassume said second condition, moving said stent to a selected second location while said stent is in said second condition, and discontinuing said flow of said cool solution, whereby said stent is caused by said body temperature to reassume said first condition to hold open said second location of said urinary passageway.

4. A method for treatment of obstructive urethra portions in a mammal, said method comprising the steps of:

inserting a cystoscope in said urethra, moving said cystoscope in said urethra to dispose a distal end of said cystoscope proximate a furthest end of the obstructive portion, measuring the length of the obstructive portion of said urethra through said cystoscope, providing a stent adapted to assume a first condition when exposed to body temperature of said mammal, and adapted to assume a second condition when exposed to a transition temperature less than said body temperature, said stent in said first condition being rigid and generally tubular in configuration, and having a selected length substantially equal to the measured length of said obstructive portion, and in said second condition being flexible and compressible to a size substantially smaller in diameter than the size of said stent in said first condition, inserting said stent in said second condition into a catheter, moving said stent to a distal end of said catheter, inserting said catheter in said cystoscope, moving said catheter through said cystoscope to position said stent adjacent said obstructive portion of said urethra;

flowing a cool solution through said catheter, said cool solution being at a temperature no more than said transition temperature, moving said stent out of said catheter and into said obstructed portion of said urethra, and discontinuing said flow of said cool solution through said catheter, whereby said stent is caused by said body temperature to assume said first condition to hold open said urethra obstructive portion.

5. The method in accordance with claim 4, including the further step of ascertaining visually the location of said stent in said first condition in said urethra, through said cystoscope.

6. The method in accordance with claim 5, including the further steps of flowing said cool solution through said stent to cause said stent to reassume said second condition, moving said stent to a selected second location in said urethra, and discontinuing said flow of said cool solution, whereby said stent is caused by said body temperature to again assume said first condition to hold open said urethra obstructed portion.

7. The method in accordance with claim 4, including the additional step of flowing a warm solution through said catheter, said warm solution being at a temperature sufficient to cause said stent to assume said first condition, whereby said stent is caused at least in part by said warm solution to assume said first condition.

8. The method in accordance with claim 6, including the additional step of flowing a warm solution through said catheter, said warm solution being at a temperature sufficient to cause said stent to assume said first condition, whereby said stent is caused at least in part by said warm solution to assume said first condition.

9. The method in accordance with claim 6, wherein said moving of said stent to said selected second location is accomplished by use of endoscopic forceps.

10. A method for treatment of obstructive prostatism in a mammal having a bladder and a urethra with a prostatic portion, said method comprising the steps of:

inserting a cystoscope in said urethra, moving said cystoscope in said urethra to dispose a distal end of said cystoscope proximate said bladder, measuring said prostatic portion of said urethra through said cystoscope, providing a stent adapted to assume a first condition when exposed to body temperature of said mammal, and adapted to assume a second condition when exposed to a transition temperature less than said body temperature, said stent in said first condition being rigid and generally tubular in configuration, and having a selected length substantially equal to the measured length of said prostatic portion, and in said second condition being flexible and compressible to a size substantially smaller in diameter than the size of said stent in said first condition, inserting said stent in said second condition into a catheter, moving said stent to a distal end of said catheter, inserting said catheter through said cystoscope to position said stent adjacent said prostatic portion of said urethra;

flowing a cool solution through said catheter, said cool solution being at a temperature no more than said transition temperature, moving said stent out of said catheter and into said prostatic portion of said urethra, and discontinuing said flow of said cool solution through said catheter, whereby said stent is caused by said body temperature to assume said first condition to hold open said urethra prostatic portion.

11. The method in accordance with claim 10, including the further step of ascertaining visually the location of said stent in said first condition in said urethra, through said cystoscope.

12. The method in accordance with claim 11, including the further steps of flowing said cool solution through said stent to cause said stent to reassume said second condition, moving said stent to a selected second location in said prostatic portion of said urethra, and discontinuing said flow of said cool solution, whereby said stent is caused by said body temperature to again assume said first condition to hold open said urethra prostatic portion.

13. The method in accordance with claim 10, including the additional step of flowing a warm solution through said catheter, said warm solution being at a temperature sufficient to cause said stent to assume said first condition, whereby said stent is caused at least in part by said warm solution to assume said first condition.

14. The method in accordance with claim 12, including the additional step of flowing a warm solution through said catheter, said warm solution being at a temperature sufficient to cause said stent to assume said first condition, whereby said stent is caused at least in part by said war solution to assume said first condition.

15. The method in accordance with claim 12, wherein said moving of said stent to said selected second location is accomplished by use of endoscopic forceps.

16. A method for treatment of obstructive ureter portions in a mammal, said method comprising the steps of:
measuring the length of the obstructive portion of the ureter,
providing a stent adapted to assume a first condition when exposed to body temperature of said mammal, and adapted to assume a second condition when exposed to a transition temperature less than said body temperature, said stent in said first condition being rigid and generally tubular in configuration, and having a selected length substantially equal to the measured length of said obstructive portion, and in said second condition being flexible and compressible to a size substantially smaller in diameter than the size of said stent in said first condition,
extending a wire between a bladder at a first end of said ureter and a renal pelvis at a second end of said ureter, said wire extending through said obstructive portion of said ureter,
placing a catheter with said stent therein in said second condition around said wire,
moving said catheter along said wire until said catheter is disposed in said obstructive portion of said ureter,
flowing a cool solution at a temperature no greater than said transition temperature through said catheter and through said stent to maintain said stent in said second condition,
separating said catheter from said stent, terminating said flow of said cool solution, and withdrawing said catheter and said wire from said ureter, leaving said stent in said obstructive portion of said ureter,
whereby said stent is caused by said body temperature to assume said first condition to hold upon said obstructive portion of said ureter.

17. The method in accordance with claim 16 wherein said wire is passed through a ureteral orifice in said bladder and to said renal pelvis.

18. The method in accordance with claim 17 wherein measuring said length of said obstructive portion of said ureter is accomplished by a pyeloureterogram.

19. The method in accordance with claim 18 including the step of inserting a cytoscope through a urethra in communication with said bladder, moving said cytoscope in said bladder to a ureteral orifice, and moving said wire through said cytoscope, through said ureteral orifice and through said ureter to said renal pelvis.

20. The method in accordance with claim 19 wherein positioning of said stent in said ureter is determined by fluoroscopy.

21. The method in accordance with claim 20 wherein said stent is releasably connected to a grasping tool, such as that said positioning of said stent is accomplished by manipulation of said grasping tool, and including the additional step of releasing said stent from said tool and withdrawing said tool.

22. The method in accordance with claim 16 and including the additional step of flowing warm solution of at least said body temperature through said catheter upon movement of said stent into said obstructive portion of said ureter, whereby said stent is caused at least in part by said warm solution to assume said first condition.

23. The method in accordance with claim 16 and including the further steps of flowing said cool solution through said stent to cause said stent to reassume said second condition, moving said stent to a selected second location in said ureter, and discontinuing said flow of said cool solution, whereby said stent is caused by said body temperature to again assume said first condition to hold open said ureter obstructive portion.

24. A method for treatment of obstructive ureter portions in a mammal, said method comprising the steps of:
moving a ureteroscope into a ureter and through said ureter to gain visual access to the obstructive portion of the ureter,
visually measuring the length of said obstructive portion of said ureter,
providing a stent adapted to assume a first condition when exposed to body temperature of said mammal, and adapted to assume a second condition when exposed to a transition temperature less than said body temperature, said stent in said first condition being rigid and generally tubular in configuration, and having a selected length substantially equal to the measured length of said obstructive portion, and in said second condition being flexible and compressible to a size substantially smaller in diameter that the size of said stent in said first condition,
placing said stent in said second condition in a catheter,
passing said catheter with said stent therein through a working channel of said ureteroscope until a distal end of said catheter is at or beyond a furthest boundary of said obstructive portion,
expelling said stent from said catheter and into said ureter in said obstructive portion,
whereby said stent is caused by said body temperature to assume said first condition to hold open said ureter obstructive portion.

25. The method in accordance with claim 24 including the additional step of flowing a warm solution through said catheter as said stent is expelled from said catheter, the warm solution being of a temperature equal to at least said body temperature, whereby said stent is cased at least in part by said warm solution to assume said first condition.

26. The method in accordance with claim 24, and including the additional step of flowing a cool solution through said catheter and through said stent, said cool solution being of a temperature no greater than said transition temperature to cause said stent to reassume said second condition, advancing endoscopic forceps through said ureteroscope to grasp said stent and move said stent in said ureter, and flowing said warm solution through said catheter.

* * * * *

UNITED STATES PATENT AND TRADEMARK OFFICE
CERTIFICATE OF CORRECTION

PATENT NO. : 5,224,953
DATED : July 6, 1993
INVENTOR(S) : Abraham Morgentaler

It is certified that error appears in the above-indentified patent and that said Letters Patent is hereby corrected as shown below:

Col. 1, line 17, after "symptoms" insert --including nocturia, urniary retention, frequent urination,--.

Col. 4, line 54, after "by" delete "Kleih" and isnert --Klein,--.

Signed and Sealed this

Twenty-second Day of February, 1994

Attest:

BRUCE LEHMAN

*Attesting Officer*  *Commissioner of Patents and Trademarks*